US00PP28021P3

(12) United States Plant Patent
Castellarin et al.

(10) Patent No.: US PP28,021 P3
(45) Date of Patent: May 16, 2017

(54) GRAPEVINE NAMED 'FLEURTAI'

(50) Latin Name: ***Vitis×vinifera* (hybrid)**
Varietal Denomination: FLEURTAI

(71) Applicants: Università degli Studi di Udine, Udine UD (IT); Istituto di Genomica Applicata, Udine UD (IT)

(72) Inventors: Simone Diego Castellarin, Vancouver (CA); Guido Cipriani, Faedis (IT); Gabriele Di Gaspero, Cividale del Friuli UD (IT); Michele Morgante, Tricesimo UD (IT); Enrico Peterlunger, Codroipo UD (IT); Raffaele Testolin, Udine (IT)

(73) Assignees: Università degli Studi di Udine, Udine (IT); Istituto di Genomica Applicata, Udine (IT)

( * ) Notice: Subject to any disclaimer, the term of this patent is extended or adjusted under 35 U.S.C. 154(b) by 0 days.

(21) Appl. No.: 14/545,111

(22) Filed: Mar. 27, 2015

(65) Prior Publication Data

US 2016/0242340 P1 Aug. 18, 2016

(30) Foreign Application Priority Data

Feb. 13, 2015 (QZ) ..... PBR 2015/0363

(51) Int. Cl.
*A01H 5/08* (2006.01)

(52) U.S. Cl.
USPC ..... Plt./207

(58) Field of Classification Search
USPC ..... Plt./207
See application file for complete search history.

*Primary Examiner* — Annette Para
(74) *Attorney, Agent, or Firm* — Foley & Lardner LLP

(57) ABSTRACT

A new and distinct variety of grapevine plant named 'FLEURTAI', primarily adapted to the growing conditions of the temperate regions and characterized by its strong vigor; erect growth habit; small to medium circular shaped leaves with medium texture; medium sized berry clusters with golden-green berries that have an amber nuance on the sunny side of the berry, soft flesh, neutral taste, and no flesh coloration primarily used for wine; early harvesting time; and resistance to winter temperatures (to −23° C.), resistance to downy mildew, and tolerance to powdery mildew.

4 Drawing Sheets

Latin name of the genus and species of the plant claimed: *Vitis×vinifera* (hybrid).

Variety name: 'FLEURTAI'.

BACKGROUND OF THE INVENTION

The present invention relates to a new and distinct summer/fall bearing grapevine variety, botanically known as *Vitis vinifera*, and hereinafter referred to by the name 'FLEURTAI'.

The new grapevine 'FLEURTAI' is a product of a controlled breeding program conducted by the inventors in Udine, Italy. The objective of the breeding program was to develop a new grapevine variety particularly characterized by resistance to cold (<−20° C.), resistance to downy mildew (*Plasmopara viticola*), and tolerance to powdery mildew (*Uncinula necator*).

The new grapevine 'FLEURTAI' originated from a cross made by the inventors in Udine, Italy. The female or seed parent is the grapevine variety, *Vitis vinifera* cv. 'Tocai Friulano' (unpatented), and the male or pollen parent is the grapevine variety, *Vitis* cv. '20/3' (Bianca×SK77-4/5) (unpatented).

The new grapevine 'FLEURTAI' was discovered and selected by the inventors as a single flowering plant within the progeny of the stated cross in a controlled environment in 2002 in Udine, Italy. Asexual reproduction of the new grapevine variety by grafting was first performed in February 2004 in Rauscedo, Friuli Venezia Giulia region, Italy, and has demonstrated that the combination of characteristics as herein disclosed for the new cultivar are firmly fixed and retained through successive generations of asexual reproduction. The new cultivar reproduces true to type.

SUMMARY OF THE INVENTION

'FLEURTAI' is primarily adapted to the climate and growing conditions of the temperate regions with average yearly temperature about 13° C., minimum winter temperature about −20° C., annual rainfall around 700-1500 mm of rain (e.g. North-Eastern Italy, Friuli). This region provides the necessary year-round temperatures required for it to produce and maintain a strong vigorous plant with consistent fruit production from April through November on primocanes and in the ensuing year from April through November on the floricanes.

The following traits have been repeatedly observed and are determined to be unique characteristics of 'FLEURTAI', which in combination distinguish this grapevine plant as a new and distinct variety.

1. Strong vigor;
2. Erect growth habit;
3. Small to medium circular shaped leaves with medium to dark green upper surfaces and light green lower surfaces and medium texture;
4. Medium size, loose to medium dense, conical berry clusters with two middle size wings; golden-green color berries with amber nuances on the sunny side of the berry, soft flesh, neutral taste, no flesh coloration; primarily for wine; maturing in late August (Middle Friuli, North-Eastern Italy);

5. Primocanes and floricanes with oblate cross section, brownish color, no lenticels, and short-middle internodes (diameter: 8 mm);
6. Late August harvesting time (Middle Friuli, North-Eastern Italy); and
7. Resistance to winter temperature (−23° C.), resistance to downy mildew, and tolerance to powdery mildew.

Plants of the new grapevine 'FLEURTAI' differ from plants of the parents, *Vitis vinifera* 'Tocai Friulano' (unpatented) and *Vitis* cross '20/3' (unpatented), in the following characteristics described in Table 1.

TABLE 1

Comparison with Parent Varieties

| Characteristic | New Cultivar 'FLEURTAI' | Female Parent 'Tocai Friulano' (unpatented) | Male Parent '20/3' (unpatented) |
|---|---|---|---|
| vigor | strong | strong | medium |
| growth habit | erect | semi-erect | semi-erect |
| leaf | small to medium size, medium to dark green color (upper surface), light green color (lower surface), no hairs in both surfaces, circular shape, medium texture | medium size, light green color (upper surface), green color (lower surface), very few hairs in both surfaces, circular shape, medium texture | Medium size, light green color (upper surface), green color (lower surface), no hairs in both surfaces, wedge-shaped—kidney-shaped, medium texture |
| cluster | very low-low weight, conical with two middle size wings, loose or medium dense, berry skin with golden-green color with amber nuances in the sunny side of berry, soft flesh, neutral taste, no flesh coloration, use: wine, maturity: early (late August, Middle Friuli, North-Eastern Italy) | low weight, conical, with 1-2 wings, dense, berry skin with green-yellow color, soft flesh, neutral taste, no flesh coloration, use: wine, maturity: medium (early September at Udine, North-Eastern Italy) | low weight, conical, with 1-2 wings, medium dense, berry skin with green-yellow color, slightly firm flesh, neutral taste, no flesh coloration, use: wine, maturity: early (late August, Middle Friuli, North-Eastern Italy) |
| primocane and floricane | oblate cross section, brownish color, lenticels: absent, short-medium internodes, diameter: small (about 8 mm) | circular cross section, brownish color, lenticels: absent, short-medium internodes, diameter small 8 mm) | oblate cross section, brownish color, lenticels: absent, medium internodes, diameter small (about (about 8 mm) |
| harvesting time | early (last decade August, Middle Friuli, North-Eastern Italy) | Early-medium (early September, Middle Friuli, North-Eastern Italy) | Early (end August, Middle Friuli, North-Eastern Italy) |
| resistances | resistant to winter temperature (−23° C.), resistant to downy mildew, tolerant to powdery mildew | Average resistance to winter temperature (−15° C.), susceptible to downy mildew, susceptible to powdery mildew | resistant to winter temperature not checked, resistant to downy mildew, resistant to powdery mildew |

Of the many commercial cultivars known to the present inventor, the most similar to the new grapevine 'FLEURTAI' is the female parent 'Tocai Friulano', to which a comparison has been provided above.

BRIEF DESCRIPTION OF THE PHOTOGRAPHS

The accompanying photographs illustrate the overall appearance of the new grapevine 'FLEURTAI' showing the colors as true as is reasonably possible with colored reproductions of this type. Colors in the photographs may differ slightly from the color values cited in the detailed botanical description, which accurately describe the color of 'FLEURTAI'.

DETAILED BOTANICAL DESCRIPTION

Figure 1A:
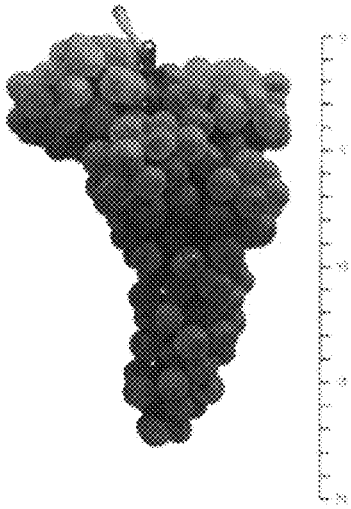
FIG. 1A and FIG. 1B show a typical fruit cluster of 'FLEURTAI' taken on Aug. 25, 2012, in Udine, Italy.
Figure 1B:
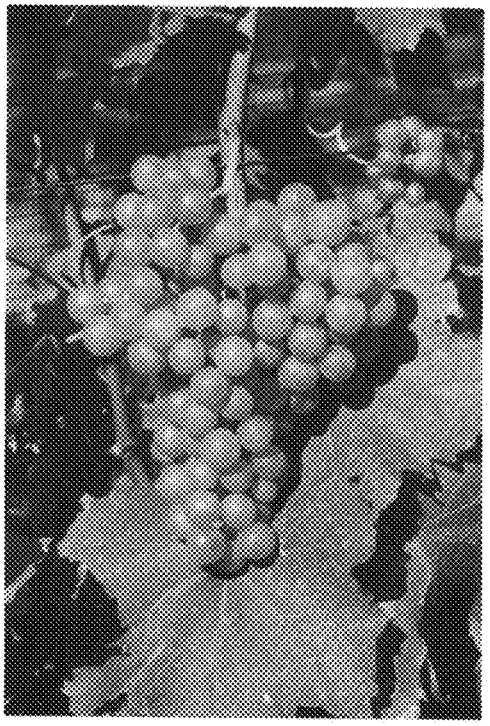
Figure 2:
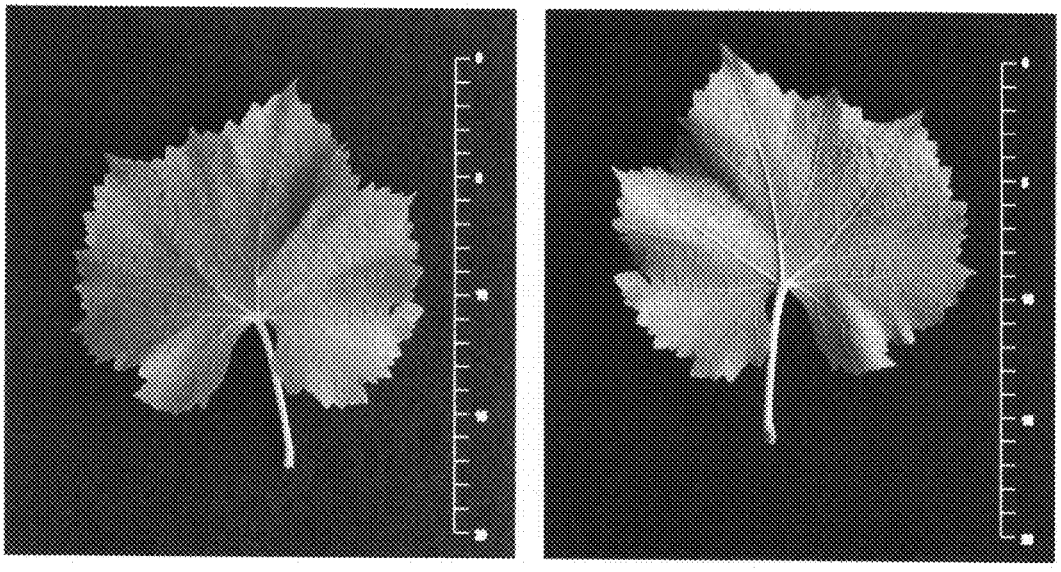
FIG. 2 shows a typical mature leaf (upper surface, left and lower surface, right) of 'FLEURTAI' taken on Jun. 15, 2012, in Udine, Italy.
Figure 3:
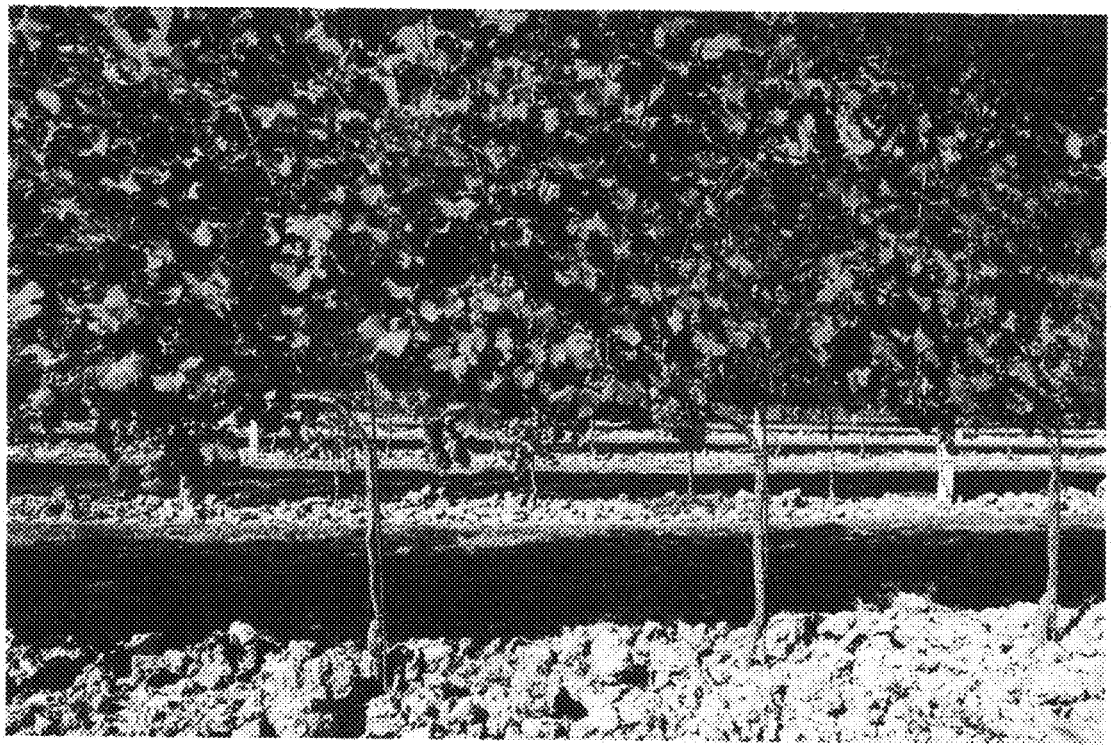
FIG. 3 shows a typical mature vine of 'FLEURTAI' taken on Aug. 3, 2012.
Figure 4:
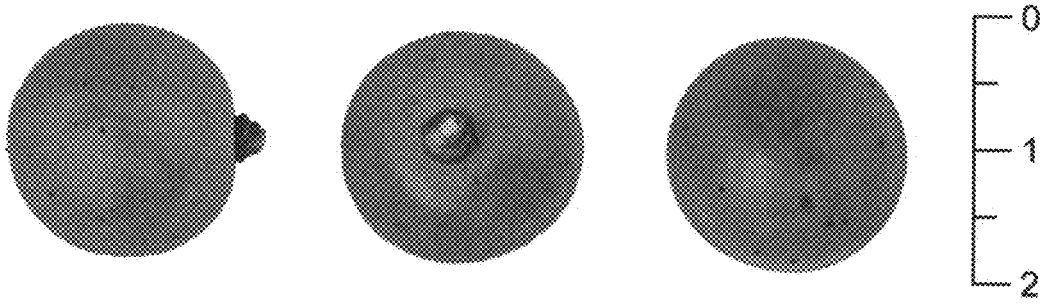
FIG. 4 shows a close-up view of typical mature fruit of 'FLEURTAI' taken on Aug. 25, 2012, in Udine, Italy

The following description of 'FLEURTAI' unless otherwise noted, is based on observations taken during the 2011, 2012, and 2013 growing seasons(s) in Udine, Italy and Fossalon di Grado (GO), Italy, from plants dug from a nursery located in Vivai Cooperativi Rauscedo, Rauscedo (PN), Italy during the beginning of December 2007 and planted approximately 16 to 20 weeks later in Udine, Italy and Fossalon di Grado (GO), Italy. The phenotypical descriptions and color designations stated for the new variety may vary, depending upon variations in environmental factors, including weather (temperature, humidity and light intensity), day length, soil type, location and cultural conditions. 'FLEURTAI' has not been observed under all possible environmental conditions.

| Characteristic | 'FLEURTAI' | 'TOCAI FRIULANO' (unpatented) |
|---|---|---|
| GENERAL | | |
| Resistance to pest/disease | Resistant to downy mildew, tolerant to powdery mildew | Susceptible to downy mildew and to powdery mildew |
| Resistance to natural elements | Resistant to winter cold down to −23° C. | Resistant to winter cold down to −15° C. |
| VINE | | |
| Vigor | strong | strong |
| Trunk diameter | 6 cm (6 yrs.-old plant) | 6.5 |
| Bark | | |
| color | RHS 177B | Dark brown |
| underbark color | RHS 179B | Light brown |
| texture | n.a. | n.a. |
| Canes | | |
| length | Internode length cm 10.5 | Internode length about cm 10 |
| width | 8 mm | 8 mm |
| Shoots | | |
| shape | Erected, cross section: oblate, surface: with stripes, nodes and internodes without hairs | Semi-erected, cross section: circular, surface: smooth, nodes and internodes without hairs |

-continued

| Characteristic | 'FLEURTAI' | 'TOCAI FRIULANO' (unpatented) |
|---|---|---|
| color | internodes with red (RHS 185B) and green (RHS144B) pigmentation on both sides, nodes with red (RHS 185B) and green (RHS144B) dorsal side and green (RHS144B) ventral side | Internodes with green color on ventral and dorsal side, nodes with green ventral and dorsal side |
| Tendrils | | |
| form | Bifid or trifid | bifid |
| color | RHS 145C | Green |
| texture | normal | normal |
| number | 2 or <2 consecutive | 2 or <2 consecutive |
| Buds | | |
| size | average | average |
| shape | round | round |
| color | RHS 139C | Light brown |
| number | 2/node | 2/node |
| time of budbreak | early | early-medium |
| LEAVES | | |
| Size | small-medium | medium |
| Number of leaflets | 5 | 5 |
| Glossiness | Medium-high | medium |
| Cross section shape | V-shaped | V-shaped |
| Color (immature) | | |
| Upper surface | RHS 140B | Light green |
| Under surface | RHS 140B | green |
| Color (mature) | | |
| Upper surface | RHS 141A | Medium green |
| Under surface | RHS 141B | Darker green |
| Petiole | | |
| Length (cm) | 6.2 | 6.0 |
| Color (upper surface) | RHS 145C | green |
| Color (under surface) | RHS 145C and RHS180A | green |
| Stipule orientation | n.a. | n.a. |
| FLOWERS | | |
| Flowering period (time of beginning of flowering) | End of May | End of May |
| Sex | hermaphrodite | hermaphrodite |
| Size | Average | average |
| Diameter (cm) | 0.3 (stamens) | 0.3 (stamens) |
| Pistil Color | RHS 149A | |
| Stamen Color | RHS 4D | |
| Fragrance | average | average |
| Flower number (at 3rd node from tip of lateral mean and range) | n.a. | n.a. |
| Petals | | |
| Length (cm) | n.a. | n.a. |
| Width (cm) | n.a. | n.a. |
| Overall shape | calyptra | calyptra |
| Calyptra Color | RHS 134A | green |

-continued

| Characteristic | 'FLEURTAI' | 'TOCAI FRIULANO' (unpatented) |
|---|---|---|
| Sepals | | |
| Length (cm) | n.a. | n.a. |
| Width (cm) | n.a. | n.a. |
| Overall shape | n.a. | n.a. |
| Color (immature) | n.a. | n.a. |
| Upper surface | | |
| Under surface | | |
| Color (mature) | n.a. | n.a. |
| Upper surface | | |
| Under surface | | |
| Pedicel | | |
| Length (mm) | 45 (cluster) | 70 |
| Color | RHS 145C | green |
| FRUIT | | |
| Primocane time of fruiting (1st pick) | August 25th | September 7th |
| Clusters | | |
| cluster weight | g 170 | g 230 |
| cluster shape | conical | conical |
| cluster length | mm 180 | medium |
| avg. berries per cluster | 200 | 220 |
| avg. clusters per shoot | 2 | 2 |
| Berries | | |
| Berry size | Very low to low (g 1.8) | Very low to low (g 1.5) |
| Berry length (cm) | 1.76 | 1.50 |
| Berry width (cm) | 1.56 | 1.50 |
| Overall shape of berry | broad ellipsoid | globose |
| Berry Texture | soft | soft |
| Berry Skin Color (immature) | RHS 137C | green |
| Berry Skin Color (mature, at 19° Bx) | RHS 4D | green |
| Berry Flesh Color | RHS 149D | |
| Soluble solids (%) | 22.6 | 21.1 |
| Titratable acidity (as g/L tartaric acid) | 4.6 | 5.7 |
| Sugar/acid ratio | 4.9 | 3.7 |
| Firmness | soft | soft |
| Seeds | 2-3 | 2-3 |
| Seed color | RHS 166C | |
| Skin cracking? | no | rarely |
| Juice color | transparent | transparent |
| Berry taste | Neutral | neutral |
| Eating quality | n.a. | n.a. |
| Berry uses | wine | wine |
| Shipping quality | n.a. | n.a. |

What is claimed is:

1. A new and distinct grapevine, referred to as 'FLEURTAI', as herein described and illustrated by the characteristics set forth above.

* * * * *